United States Patent [19]
Shepard et al.

[11] 4,051,189
[45] Sept. 27, 1977

[54] CYCLIC ETHERS OF PHENOLIC COMPOUNDS AND POLYMERS THEREOF

[75] Inventors: Alvin F. Shepard; Bobby F. Dannels, both of Grand Island, N.Y.

[73] Assignee: Hooker Chemicals & Plastics Corporation, Niagara Falls, N.Y.

[21] Appl. No.: 711,651

[22] Filed: Aug. 4, 1976

Related U.S. Application Data

[63] Continuation of Ser. No. 570,545, April 22, 1975, abandoned, which is a continuation-in-part of Ser. No. 450,945, March 13, 1974, abandoned.

[51] Int. Cl.$^2$ .................... C07C 37/00; C07C 39/16
[52] U.S. Cl. .................... 260/619 A; 260/340.3; 424/278
[58] Field of Search .................... 260/619 A

[56] References Cited
U.S. PATENT DOCUMENTS

| | | | |
|---|---|---|---|
| 2,499,367 | 3/1950 | DeGroote et al. | 260/619 A |
| 2,499,370 | 3/1950 | DeGroote et al. | 260/619 A |
| 2,730,551 | 1/1956 | Beaver et al. | 260/619 A |
| 2,905,737 | 9/1959 | Webb | 260/619 A |
| 3,151,096 | 9/1964 | Kordyinski et al. | 260/619 A |
| 3,244,671 | 4/1966 | Shepard | 260/619 A |
| 3,378,518 | 4/1968 | Doyle | 260/619 A |
| 3,409,571 | 11/1968 | Shepard et al. | 260/17.2 |
| 3,697,459 | 10/1972 | Dannels et al. | 260/17.2 |
| 3,737,465 | 6/1973 | Karll et al. | 260/619 A |
| 3,876,620 | 4/1975 | Moss | 260/619 A |

Primary Examiner—Norman Morgenstern
Attorney, Agent, or Firm—Peter F. Casella; James F. Mudd; Howard M. Ellis

[57] ABSTRACT

This invention relates to novel aromatic compounds and to novel aromatic polymers of the compounds. The compounds of the present invention are cyclic ethers of orthobisphenol having the following structure:

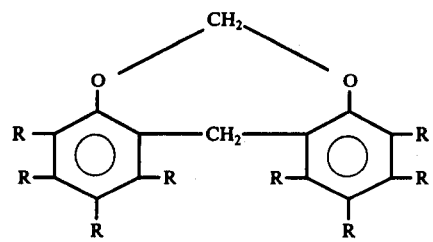

wherein R is independently selected from the group of hydrogen, chlorine, bromine or fluorine. The compounds of the present invention may be easily polymerized and the polymers exhibit good stability at high temperatures. The polymers are useful as molding compounds in applications where phenol-aldehyde and phenol-ketone condensates are now used.

3 Claims, No Drawings

CYCLIC ETHERS OF PHENOLIC COMPOUNDS AND POLYMERS THEREOF

This is a continuation of application Ser. No. 570,545, filed Apr. 22, 1975, which is a continuation-in-part of Ser. No. 450,945, filed Mar. 13, 1974, both now abanonded.

The present invention relates to new cyclic ethers or ortho bisphenol and are produced by reacting a molar excess of orthobisphenol with bifunctional alkylene or alkylidene compound. It would be expected that such reaction would yield polymeric ethers, however, the products of the reaction are found to be a simple monomeric cyclic ether. The process is a condensation process and is carried out using an alkali metal or alkali metal hydroxide as a reactant, for example, sodium, potassium, or their hydroxide. The amount of alkali metal hydroxide used is generally between about 180 and 240 mole percent of the bisphenol utilized. Although additional amounts of alkali metal hydroxide may be used, the reaction is not proportionally speeded and additional subsequent removal problems will be encountered. The use of less than about 180% alkali metal hydroxide is operative, at a slower rate, however, the present process is not a rapid one and slowing the reaction does not appear to be advantageous.

The ethers of the present invention may be characterized by the following formula:

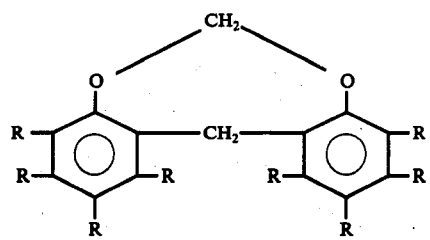

wherein R is independently selected from the group of hydrogen, chlorine, bromine and fluorine.

The bifunctional alkylene or alkylidene compound utilized as a reactant, is suitably a dihalogen derivative such as dibromomethane or dichloromethane.

The reaction is effected by the formation of the corresponding alkali metal halide together with the ether product. The reaction may conveniently be carried out at atmospheric pressure and reflux temperatures. Under these conditions the time required for the reaction to go to completion varies with the reactants and their concentration, but may be as long as eight days. Such reaction may be illustrated:

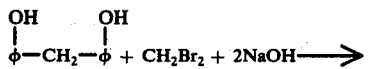

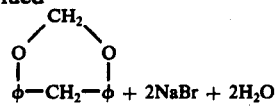

Although the compounds per se, are useful in molding compounds, and in the preparation of polymers, particularly polymers which require high temperature stability, the halogenated compounds of the present invention have the added attribute of fire-retardant properties and are also useful as fire-retardant additives in plastic compositions. Further, the cyclic methyl ether of hexachlorophene:

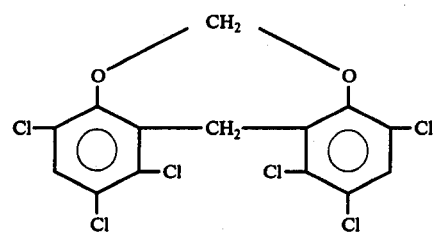

is found to have strong bactericidal power, similar to hexachlorophene. The methylene ether is soluble in various liquids which are poor solvents for hexachlorophene and are useful in the preparation of new bactericidal mixtures.

The cyclic ethers of the present invention may be easily polymerized using known techniques by reaction in the presence of a polymerization catalyst if either the R in the ortho or para positions of the phenol groups is hydrogen. Preferably, the R in the ortho position is hydrogen. Catalysts found most effective are $BF_3$, $BCl_3$ and $PF_5$. A catalyst range of from 0.5 to 25% by weight of the methylene ether has been found useful. Suitably the polymerization reaction is carried out in an inert solvent such as hexane. The ether is initially mixed with the solvent, air removed, and the catalyst added. The reaction is suitably carried out at ambient temperature and pressure. The polymer products of the present invention may be characterized by the following formula:

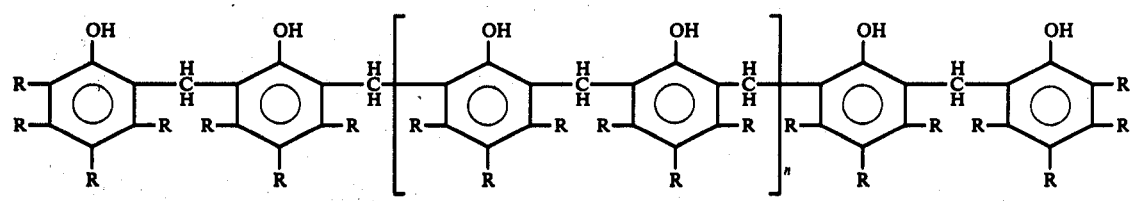

wherein R is independently selected from the group consisting of hydrogen, chlorine, bromine and fluorine and n is at least 5 and averages between about 30 and about 300.

The following examples, while not limiting, will illustrate various aspects of the invention. Unless otherwise specified, temperatures are given in degrees centigrade and parts are by weight.

EXAMPLE 1

Preparation of Cyclic Methylene Ether of 0, 0'-Bisphenyl F

Into a stirred reactor there was placed 100 parts of 0,0'-bisphenol F and 500 parts of ethylene glycol dimethylether. After heating to 85° C, 20 parts of sodium, which had been cut into small pieces, was slowly added. After all the sodium had reacted, 44 parts of $CH_2Br_2$ was slowly added and the mixture was heated at 85° C for 18 hours. The reaction mixture was then poured into 2000 parts of water. The resulting solids were filtered and dried. They amounted to 40 parts and melted at 105°–107° C. The reacted bisphenol was recovered from the aqueous phase by acidification and extraction with ether.

The crude product was recrystallized from a 50/50 mixture of ethanol and water. It melted at 107°–109° C and had the following analysis: C 79.28%; H 5.11%; MW 214; calculated for the cyclic methylene ether: C 79.2%; H 5.7%; MW 212. The NMR and IR spectra showed that the cyclic structure had been formed.

EXAMPLE 2

Preparation of Cyclic Methylene Ether and 0,0'-Bisphenol F

Into a stirred reactor there was placed 50 parts of 0,0'-bisphenol F, 200 parts of 10% aqueous NaOH and 87 parts of $CH_2Br_2$. This mixture was heated to reflux (90° C) and reacted for 20 hours. An additional 8 parts of $CH_2Br_2$ was added and heating was continued for 20 more hours. The cooled reaction mixture was then poured into 2000 parts of water. The insoluble material was taken up in ether and the resulting solution washed with 5% aqueous NaOH until all unreacted bisphenol was removed. Evaporation of the solvent gave 42 parts of product that melted at 105–107. This was further purified by distillation (b.p. 112°–114° C/0.1 mm) and crystallization from 50/50 ethanol water. The final product melted at 109°–111° C.

EXAMPLE 3

Preparation of Cyclic Ether of Hexachlorophene

A solution of 1007 parts of hexachlorophene in 10000 parts of ethylene glycol dimethyl ether was placed in the stirred reactor. This was heated to 80° C and 113 parts of sodium which had been cut into small pieces was slowly added. After the sodium had reacted, 435 parts of $CH_2Br_2$ was added dropwise. The reaction was then held at 80° C for eight days. After cooling, the reaction mixture was poured into water and the resulting solids were taken up in hexane. The produce was separated from less soluble material by fractional crystallization. It was further purified by crystallization from a 75/25 mixture of hexane and ethylene glycol dimethyl ether and melted at 215°–219° C. A MW of 447 was found; theory, 419. Infrared spectra showed the absence of a band due to OH and the presence of an ether group, thus proving the cyclic ether structure.

EXAMPLE 4

Polymerization of Methylene Ether of 0,0'-Bisphenol F

A solution of 15 parts of the product of Example 2 in 1050 parts of hexane was placed in a small vessel. This was then evacuated, with some solvent flashing off, to remove air. Approximately 2 parts of $BF_3$ was then introduced. Polymer slowly precipitated from solution. After 16 hours, the solvent was decanted and the polymer was washed with a dilute $NaHCO_3$ solution. It was a high melting solid. Its infrared and NMR spectra indicated the presence of phenolic nuclei linked together by methylene groups.

EXAMPLE 5

Polymerization of Methylene Ether of 0,0'-Bisphenol F

The $BF_3$ of Example 5 was replaced by $BCl_3$. Polymer was recovered by evaporation of the solvent. Its infrared and NMR spectra indicated the presence of phenolic nuclei linked together by methylene groups in 0,0'-positions.

EXAMPLE 6

Polymerization of the Methylene Ether of 0,0'-Bisphenol F $PF_5$ was used as the catalyst in place of the $BF_3$. The product was a high melting solid.

While the present invention has been described with reference to certain specific embodiments, it will be recognized by those skilled in the art that many variations are possible without departing from the spirit and scope of the invention.

What is claimed is:

1. The method of preparing a polymer by reaction of the monomer

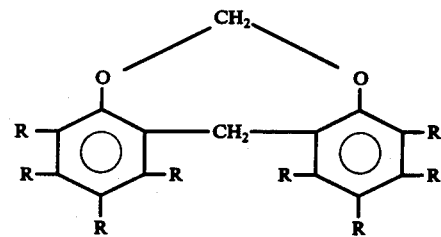

in the presence of a polymerization catalyst selected from the group consisting of $BF_3$, $BCl_3$ or $PF_5$ to form

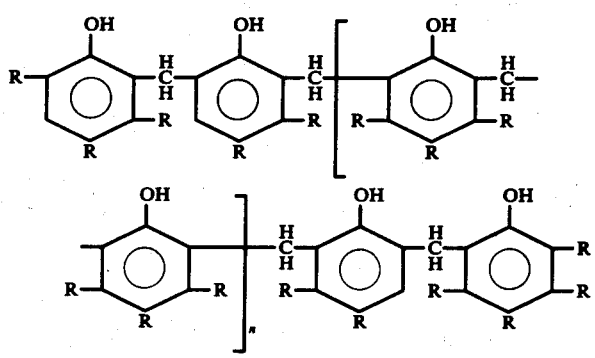

wherein R in both formulas is independently selected from the group of hydrogen, chlorine, bromine and fluorine and n is at least 5.

2. The method of claim 1 wherein the catalyst range is from about 0.5 to about 25.0 percent by weight of the monomer.

3. The method of claim 1 wherein the reaction is carried out in an inert solvent comprising hexane.

* * * * *